United States Patent
Budzelaar et al.

(10) Patent No.: US 9,662,170 B2
(45) Date of Patent: May 30, 2017

(54) SENSING APPARATUS FOR SENSING AN OBJECT

(75) Inventors: Franciscus Paulus Maria Budzelaar, Eindhoven (NL); Nenad Mihajlovic, Eindhoven (NL); Antonius Johannes Josephus Rademakers, Eindhoven (NL); Cornelius Antonius Nicholaas Maria Van Der Vleuten, Liempde (NL)

(73) Assignee: Koninklijke Philips N.V., Eindhoven (NL)

(*) Notice: Subject to any disclaimer, the term of this patent is extended or adjusted under 35 U.S.C. 154(b) by 529 days.

(21) Appl. No.: 13/885,474

(22) PCT Filed: Nov. 3, 2011

(86) PCT No.: PCT/IB2011/054879
§ 371 (c)(1),
(2), (4) Date: May 15, 2013

(87) PCT Pub. No.: WO2012/066446
PCT Pub. Date: May 24, 2012

(65) Prior Publication Data
US 2013/0231562 A1    Sep. 5, 2013

(30) Foreign Application Priority Data

Nov. 18, 2010 (EP) ..................................... 10191687
Apr. 27, 2011 (EP) ..................................... 11163796

(51) Int. Cl.
*A61B 18/14* (2006.01)
*A61B 8/12* (2006.01)
(Continued)

(52) U.S. Cl.
CPC ........ *A61B 18/1492* (2013.01); *A61B 8/0883* (2013.01); *A61B 8/12* (2013.01);
(Continued)

(58) Field of Classification Search
CPC .... A61B 8/14; A61B 8/08; A61B 8/12; A61B 5/04; A61B 2019/4036;
(Continued)

(56) References Cited

U.S. PATENT DOCUMENTS 4,706,681 A * 11/1987 Breyer et al. .................. 600/374
6,776,758 B2    8/2004 Peszynski et al.
(Continued)

FOREIGN PATENT DOCUMENTS

CN      201194837 Y    2/2009
GB      2469867        11/2010
(Continued)

OTHER PUBLICATIONS

Grainger, General Cable, RG 58/U Type Coaxial Cable specification Sheet, http://www.grainger.com/ec/pdf/General-Cable-Coaxial-Cable-RG-58U-Type-Product-Data-Sheet.pdf.*

*Primary Examiner* — Long V Le
*Assistant Examiner* — Katherine McDonald

(57) ABSTRACT

The invention relates to a sensing apparatus for sensing an object. The sensing apparatus comprises an ultrasound unit (11) for ultrasonically sensing the object (4), an electrical energy application unit (9) for applying electrical energy to the object (4), and an ultrasound unit shielding element (16) for electrically shielding the ultrasound unit (11), wherein the ultrasound unit shielding element (16) is electrically connected to the electrical energy application unit (9). Since the ultrasound unit shielding element electrically shields the ultrasound unit, the ultrasound sensing of the object is less influenced by a capacitive coupling of the application of electrical energy, in particular, of an RF signal which may be used for applying the electrical energy, into the ultrasound sensing. A further reduction of this influence is achieved by (Continued)

Figure 3:
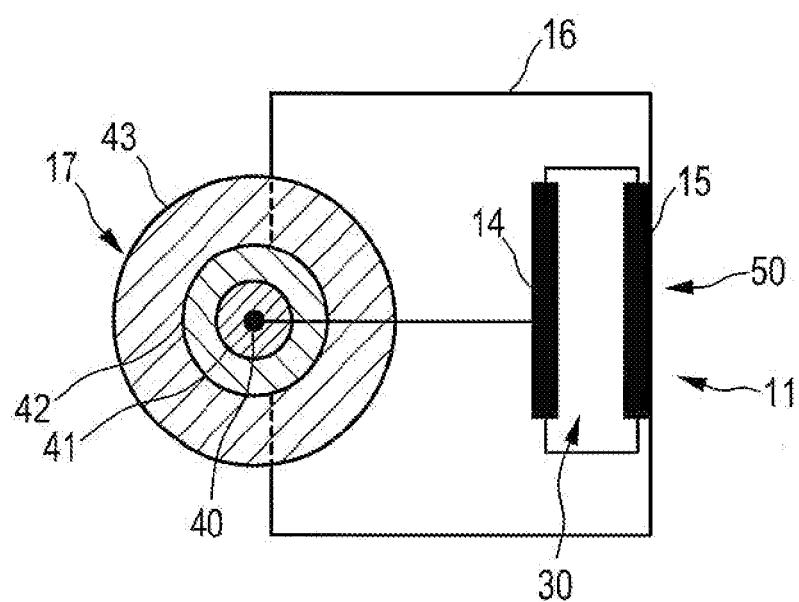

electrically connecting the ultrasound unit shielding element to the electrical energy application unit.

12 Claims, 6 Drawing Sheets

(51) Int. Cl.
*A61B 8/08* (2006.01)
*A61B 18/00* (2006.01)
*A61B 5/00* (2006.01)
*A61B 8/00* (2006.01)

(52) U.S. Cl.
CPC .............. *A61B 8/445* (2013.01); *A61B 8/486* (2013.01); *A61B 5/7217* (2013.01); *A61B 8/4494* (2013.01); *A61B 2018/00357* (2013.01); *A61B 2018/00577* (2013.01); *A61B 2018/00589* (2013.01); *A61B 2562/182* (2013.01)

(58) Field of Classification Search
CPC .. A61B 2018/00577; A61B 2018/1497; A61B 18/02; A61B 18/14; A61B 18/04; A61N 1/05; A61N 7/02
USPC .................................................. 600/466, 471
See application file for complete search history.

(56) References Cited

U.S. PATENT DOCUMENTS

| | | |
|---|---|---|
| 6,829,509 B1 | 12/2004 | MacDonald et al. |
| 7,454,974 B2 | 11/2008 | May |
| 7,520,856 B2 * | 4/2009 | Vaezy et al. .................. 600/439 |
| 7,735,349 B2 | 6/2010 | Hochmitz |
| 8,353,839 B2 | 1/2013 | Scheirer et al. |
| 2003/0004505 A1 * | 1/2003 | Bencini .............. A61B 18/1492 |
| | | 606/41 |
| 2006/0084397 A1 | 4/2006 | Turner et al. |
| 2007/0232893 A1 * | 10/2007 | Tanioka ............... A61B 5/0066 |
| | | 600/407 |
| 2009/0326529 A1 | 12/2009 | Brace et al. |

FOREIGN PATENT DOCUMENTS

| | | |
|---|---|---|
| JP | 02206444 | 8/1990 |
| JP | 2006130164 A | 5/2006 |
| WO | WO9517131 | 6/1995 |
| WO | WO9822179 | 5/1998 |
| WO | WO2005112775 | 12/2005 |
| WO | WO2010082146 | 7/2010 |

\* cited by examiner

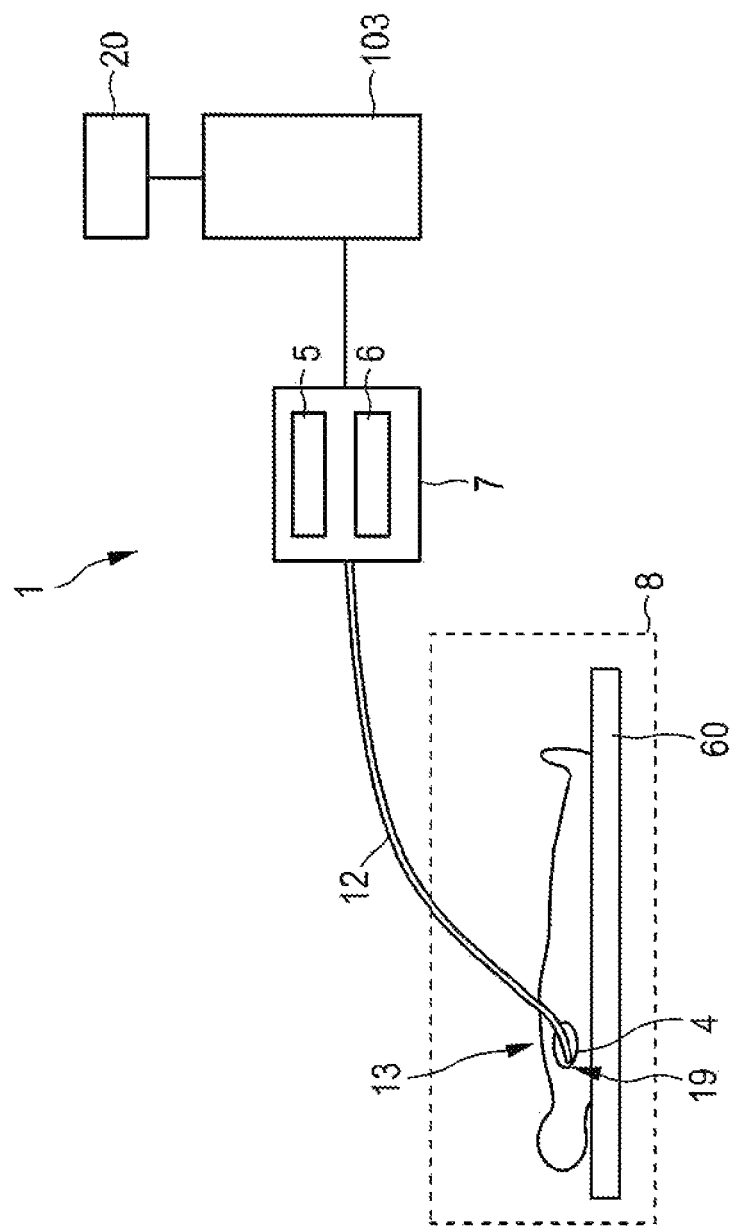

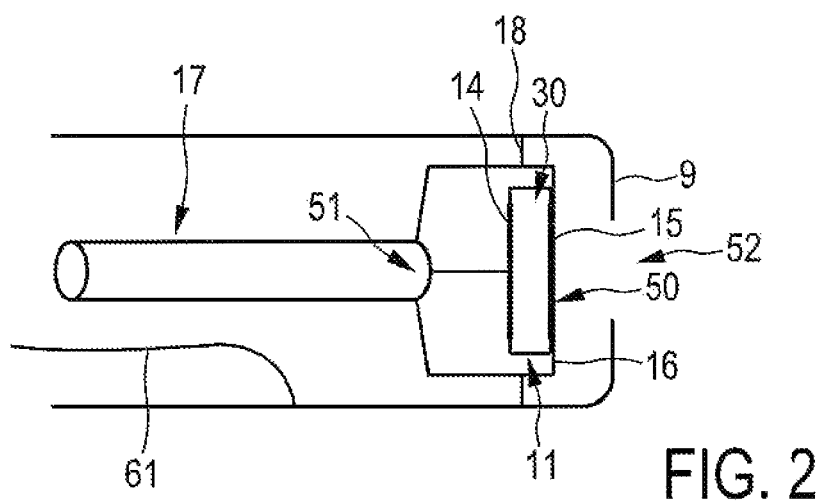
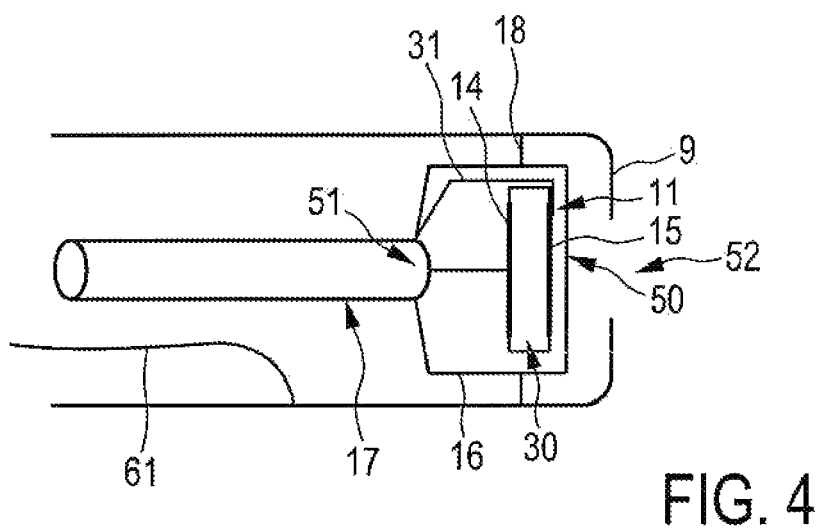

SENSING APPARATUS FOR SENSING AN OBJECT

FIELD OF THE INVENTION

The invention relates to a sensing apparatus, a sensing method and a sensing computer program for sensing an object.

BACKGROUND OF THE INVENTION

CN 201194837 Y discloses an ablation apparatus comprising a radiofrequency (RF) ablation electrode and an ultrasound unit. The ultrasound unit is used to ultrasonically sense target tissue before and/or during performing an RF ablation procedure. If the target tissue is ultrasonically sensed while the RF ablation procedure is performed, the ultrasound sensing is adversely affected by the RF energy applied to the target tissue, whereby the quality of sensing the target tissue can be reduced.

SUMMARY OF THE INVENTION

It is an object of the present invention to provide a sensing apparatus, a sensing method and a sensing computer program for sensing an object, wherein the quality of sensing the object can be improved.

In a first aspect of the present invention a sensing apparatus for sensing an object is presented, wherein the sensing apparatus comprises:

an ultrasound unit for ultrasonically sensing the object, an electrical energy application unit for applying electrical energy to the object, an ultrasound unit shielding element for electrically shielding the ultrasound unit, wherein the ultrasound unit shielding element is electrically connected to the electrical energy application unit.

Since the ultrasound unit shielding element electrically shields the ultrasound unit, the ultrasound sensing of the object is less influenced by a capacitive coupling of the application of electrical energy, in particular, of an RF signal used for applying the electrical energy, into the ultrasound sensing. A further reduction of this influence is achieved by electrically connecting the ultrasound unit shielding element to the electrical energy application unit, because this electrical connection prevents an unwanted potential difference between the ultrasound unit shielding element and the electrical energy application unit, which could result in highly non-uniform electric field distributions between the electrical energy application unit and the ultrasound unit, which could still penetrate the ultrasound unit shielding element. The ultrasound unit shielding element and, in addition, the electrical connection between the ultrasound unit shielding element and the electrical energy application unit reduce therefore an adverse influence of the application of electrical energy on the ultrasound sensing, thereby improving the quality of sensing the object.

The object is preferably a heart of a person or of an animal, in particular, cardiac tissue of a heart wall, wherein the ultrasound unit is adapted to ultrasonically sense the cardiac tissue and the electrical energy application unit is adapted to apply electrical energy to the cardiac tissue.

It is preferred that the sensing apparatus comprises a catheter, wherein the ultrasound unit, the electrical energy application unit and the ultrasound unit shielding element are integrated in the catheter. The ultrasound unit, the electrical energy application unit and the ultrasound unit shielding element can be located within or on the catheter, in particular, within or within the tip of the catheter. This allows the sensing apparatus to sense an inner part of an object like an inner heart wall or an inner wall of another object like another organ, another part of a person or of an animal like a vessel, or an inner wall of a technical object like a pipeline.

The ultrasound unit is preferentially an ultrasound transducer, which is operable at a central frequency being higher than 10 MHz. For example, the ultrasound transducer may be operable at a central frequency of about 20 MHz.

It is further preferred that the electrical energy application unit is an electrode for applying electrical energy to the object, wherein the electrode is electrically connected to the ultrasound unit shielding element. The electrical energy application unit is preferentially adapted for ablating an object, in particular, the heart of a person, and the electrode is preferentially an ablation electrode located at the tip of a catheter. The ultrasound unit shielding element is therefore preferentially electrically connected to the ablation electrode. Unwanted potential differences, which could result in highly non-uniform electrical field distributions between the ablation electrode and the ultrasound unit, which could still penetrate the ultrasound unit shielding element, can thereby be reduced, in particular, prevented.

If is also preferred that the ultrasound unit comprises at least two connection electrodes, wherein a first connection electrode is electrically connected to a control electrical connection for connecting the ultrasound unit with an ultrasound control unit for controlling the ultrasound unit and a second electrode of the ultrasound unit is electrically connected to an electrical connection shielding element for shielding the control electrical connection. The electrical connection is preferentially a coaxial cable, wherein the control electrical connection is the core of the coaxial cable and the electrical connection shielding element is preferentially the shielding of the coaxial cable. The ultrasound unit is preferentially an ultrasound transducer having a piezo material, wherein preferentially the core of the coaxial cable is electrically connected to a first electrode of the piezo material and the shielding of the coaxial cable is electrically connected to the shielding of the ultrasound transducer. This further reduces the influence of the application of electrical energy on the ultrasound sensing and, thus, further improves the quality of ultrasonically sensing the object.

In an embodiment, the electrical connection shielding element has a resistance being smaller than 5Ω. This relatively small resistance of the electrical connection shielding element, in particular, of the shielding element of the coaxial cable, can lead to a relatively low voltage across the electrical connection shielding element, even if electromagnetic interference caused by the application of energy introduces currents through the electrical connection shielding element.

In a preferred embodiment, the ultrasound unit comprises at least two connection electrodes, wherein a first connection electrode is electrically connected to a control electrical connection for connecting the ultrasound unit with an ultrasound control unit for controlling the ultrasound unit and a second electrode of the ultrasound unit is electrically connected to the ultrasound unit shielding element.

The second electrode of the ultrasound unit and the ultrasound unit shielding element can be formed as one piece, i.e. the second electrode can be formed as the ultrasound unit shielding element, or the second electrode and the ultrasound unit shielding element can be formed as electrically connected separate pieces. In particular, the second electrode of the ultrasound unit is preferentially connected to the electrical connection shielding element via the ultrasound unit shielding element.

The control electrical connection, in particular, the core of the coaxial cable, is preferentially not electrically connected with the ultrasound unit shielding element.

It is also preferred that the ultrasound unit shielding element is a housing enclosing the ultrasound unit for electrically shielding the ultrasound unit. The housing is preferentially made of an electrically conductive material like metal. The housing is, for example, a rectangular or cylindrical box enclosing the ultrasound unit. The housing can comprise an opening for allowing the control electrical connection, in particular, the coaxial cable to be introduced into the housing for electrically connecting the ultrasound unit with the ultrasound control unit.

It is further preferred that the ultrasound unit and the housing are arranged such that ultrasound waves are emittable and/or receivable through an ultrasound region of the housing. In a preferred embodiment, the ultrasound unit is operable at an ultrasound frequency defining an ultrasound wavelength in the ultrasound region of the housing, wherein at least in the ultrasound region the housing has a wall with a thickness being smaller than a quarter of the ultrasound wavelength. The ultrasound wavelength is, for example, in the order of 40 μm, wherein the thickness is preferentially smaller than 10 μm, further preferred smaller than 1 μm, and even further preferred smaller than 500 nm. In an embodiment, the thickness is about 120 nm. This reduces the probability that a part of the acoustical wave, i.e. of the ultrasound wave, is reflected back and not coupled into the object. Preferentially, the ultrasound region has a thickness being small enough to prevent any reflection of the acoustic wave. This further improves the quality of ultrasonically sensing the object.

It is further preferred that the ultrasound region is mechanically connected with the ultrasound unit. In particular, an electrode of the ultrasound unit can be mechanically connected with the ultrasound region of the housing. For example, the electrode of the ultrasound unit, which is electrically connected to the electrical connection shielding element can be mechanically connected with the ultrasound region of the housing. In an embodiment, the ultrasound region of the housing and the electrode of the ultrasound unit electrically connected to the electrical connection shielding element can be formed as one piece. The mechanical contact can improve the transmission of the acoustic waves and, thus, further improve the quality of ultrasonically sensing the object.

It is also preferred that the sensing apparatus comprises an object influence determination unit for determining the influence of the energy application on the object depending on the ultrasound sensing of the object. It is further preferred that the energy application unit is adapted to ablate the object, wherein the object influence determination unit is adapted to determine an ablation depth depending on the ultrasound sensing of the object. For example, the object influence determination unit can be adapted to determine the progression of the lesion boundary based on an M-mode image generated by ultrasonically sensing the object. Since the ultrasound sensing is only a little influenced by the application of energy to the object for ablating the same, or since the ultrasound sensing is not affected at all by the application of energy, the progression of the lesion boundary can be monitored with high quality, thereby allowing high quality monitoring of the ablation procedure based on the ultrasound sensing.

In a further aspect of the present invention a sensing method for sensing an object is presented, wherein the sensing method comprises:
ultrasonically sensing the object by an ultrasound unit,
applying electrical energy to the object by an electrical energy application unit,
wherein an ultrasound unit shielding element, which is electrically connected to the electrical energy application unit, electrically shields the ultrasound unit.

In a further aspect of the present invention a sensing computer program for sensing an object is presented, wherein the sensing computer program comprises program code means for causing a sensing apparatus as defined in claim 1 to carry out the steps of the sensing method as defined in claim 13, when the computer program is run on a computer controlling the sensing apparatus.

It shall be understood that the sensing apparatus of claim 1, the sensing method of claim 13, and the sensing computer program of claim 14 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

BRIEF DESCRIPTION OF EMBODIMENTS

Figure 5:
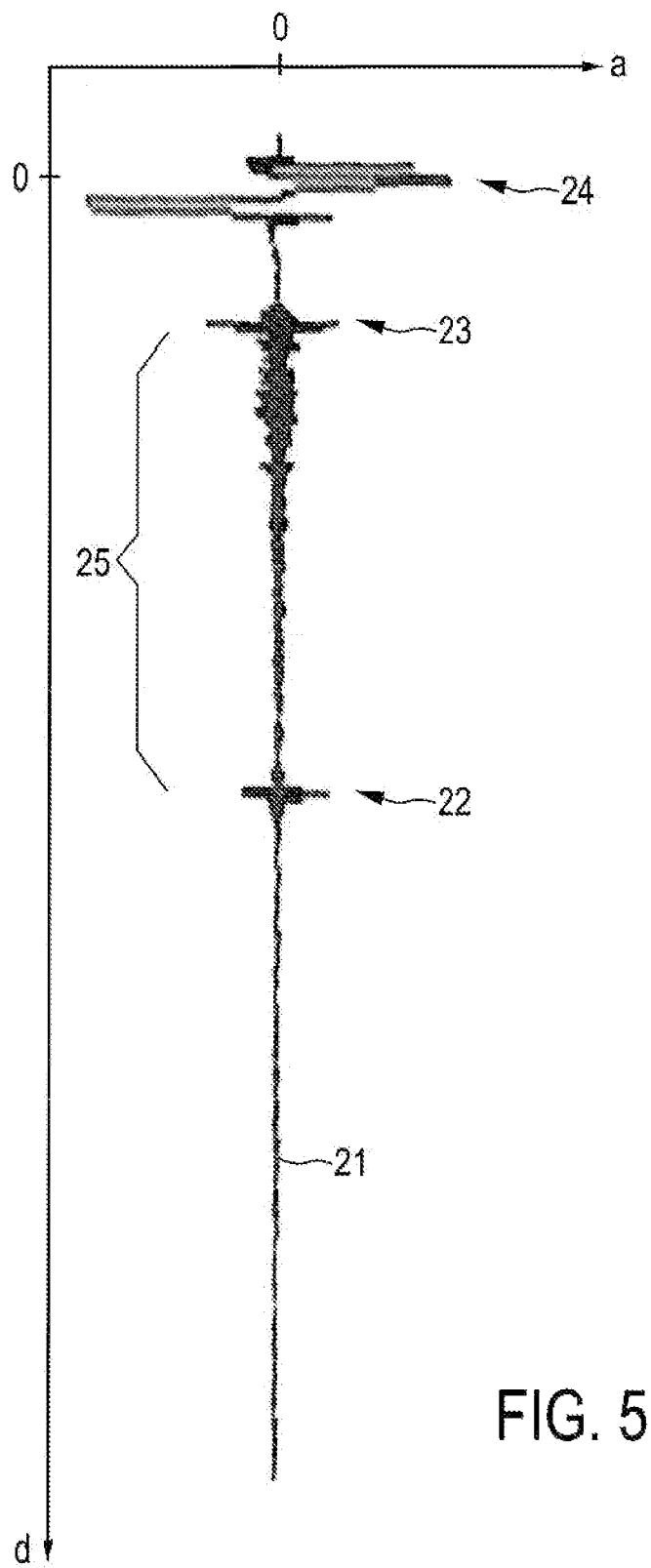
Figure 6:
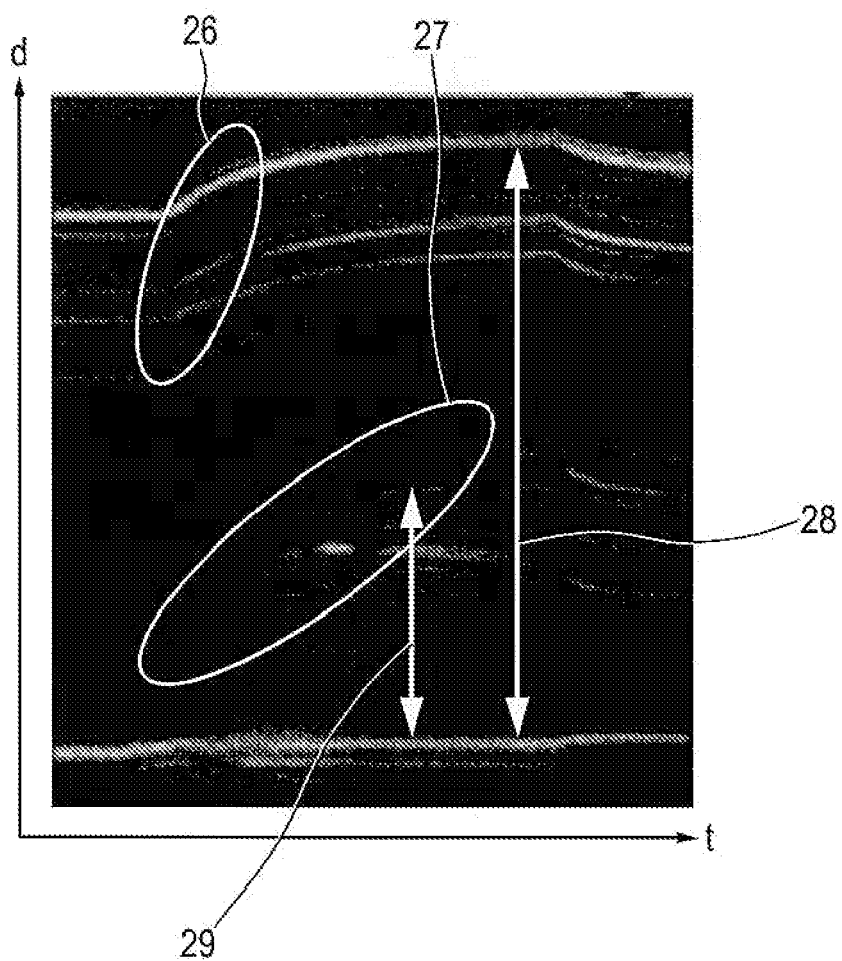
Figure 7:
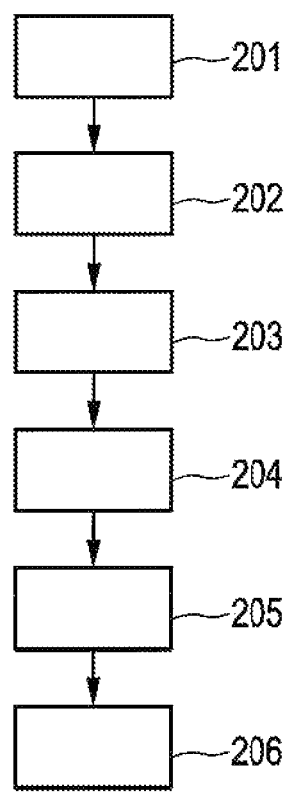

FIG. 1 shows schematically and exemplarily an embodiment of a sensing apparatus for sensing an object, FIG. 2 shows schematically and exemplarily an embodiment of a catheter tip of the sensing apparatus, FIG. 3 shows schematically and exemplarily electrical connections of elements of the catheter tip, FIG. 4 shows schematically and exemplarily another embodiment of a catheter tip of the sensing apparatus, FIG. 5 shows schematically and exemplarily a representation of an echo series produced by reflections of an ultrasound pulse at heart wall tissue, FIG. 6 shows schematically and exemplarily a two-dimensional representation of an ultrasound signal that depends on dynamic echo series, and FIG. 7 shows a flowchart exemplarily illustrating an embodiment of a sensing method for sensing an object.

DETAILED DESCRIPTION OF PREFERRED EMBODIMENTS

FIG. 1 shows schematically and exemplarily a sensing apparatus 1 for sensing an object 4. In this embodiment, the object 4 is a heart of a person 13 located on a table 60. In particular, the object is cardiac tissue of a wall of the heart 4. The sensing apparatus 1 comprises a catheter 12 with a catheter tip 19, which is schematically and exemplarily shown in more detail in FIG. 2.

The catheter tip 19 comprises an ultrasound unit 11 for ultrasonically sensing the cardiac tissue, an electrical energy application unit 9 for applying electrical energy to the cardiac tissue, and an ultrasound unit shielding element 16 for electrically shielding the ultrasound unit 11, wherein the ultrasound unit shielding element 16 is electrically connected to the electrical energy application unit 9 via an electrical connection 18.

The ultrasound unit 11 is controlled by an ultrasound control unit 5, wherein the ultrasound unit 11 and the ultrasound control unit 5 are adapted to send out ultrasound pulses into the cardiac tissue, to receive dynamic echo series after the ultrasound pulses have been reflected by the cardiac tissue and to generate an ultrasound signal depending on the received dynamic echo series. The ultrasound unit 11 is connected with the ultrasound control unit 5 via a coaxial cable 17 which is also located within the catheter 12. The electrical connection of the ultrasound unit 11 to the coaxial cable 17 is schematically shown in more detail in FIG. 3.

The ultrasound unit 11 comprises a first connection electrode 14 being electrically connected to a control electrical connection 40, which is the core of the coaxial cable 17. The ultrasound unit 11 further comprises a second electrode 15 opposite to the first electrode 14, wherein the second electrode 15 is electrically connected to an electrical connection shielding element 42 being the electromagnetic shielding of the coaxial cable 17. The coaxial cable 17 further comprises an inner dielectric insulator 41 between the core 40 and the electromagnetic shielding 42, and an outer insulating sheath being, in this embodiment, an outer plastic sheath. The core of the coaxial cable 17 and the electrical connection shielding element 42 of the coaxial cable 17 are preferably made of metal, for example, made of copper.

The ultrasound unit 11 is an ultrasound transducer comprising a piezo material 30, wherein the two electrodes 14 and 15 are located on opposite sides of the piezo material 30.

The electrical connection shielding element 42 has a resistance being smaller than 5Ω.

The second electrode 15 of the ultrasound unit 11 is connected to the electromagnetic shielding 42 of the coaxial cable 17 via the ultrasound unit shielding element 16. The second electrode 15 of the ultrasound unit 11 and the ultrasound unit shielding element 16 can be formed as one piece, i.e. the second electrode 15 can be formed as the ultrasound unit shielding element 16, or the second electrode 15 and the ultrasound unit shielding element 16 can be formed as electrically connected separate pieces. The control electrical connection 40, i.e. the core of the coaxial cable 17, is not electrically connected with the ultrasound shielding element 16.

The ultrasound unit shielding element 16 is a housing enclosing the ultrasound unit 11 for electrically shielding the ultrasound unit 11. The housing 16 is made of an electrically conductive material like metal. Preferentially, the housing 16 is a rectangular or cylindrical box enclosing the ultrasound unit 11. The housing 16 comprises an opening 51 in which the coaxial cable 17 is introduced for electrically connecting the ultrasound unit 11 with the ultrasound control unit 5.

The ultrasound unit 11 and the housing 16 are arranged such that ultrasound waves are emittable and/or receivable through an ultrasound region 50 of the housing 16. The ultrasound unit 11 is operable at an ultrasound frequency, i.e. a center frequency, of 20 MHz defining an ultrasound wavelength in the ultrasound region of the housing, wherein at least in the ultrasound region 50 the housing 16 has a wall with a thickness being smaller than a quarter of the ultrasound wavelength. The thickness of the wall of the housing 16 in the ultrasound region 50 is preferentially smaller than 10 µm, further preferred smaller than 1 µm, and even further preferred smaller than 500 nm. In this embodiment, the thickness is about 120 nm.

Referring again to FIG. 2, the electrical energy application unit 9 is an ablation electrode for applying electrical RF energy to the cardiac tissue, wherein the ablation electrode 9 is electrically connected to the housing 16 via an electrical connection 18. The ablation electrode 9 is a cap electrode provided at the tip 19 of the catheter 12 and comprises a frontal, central opening 52 for allowing the ultrasound unit 11 to sense the cardiac tissue through the opening 52. The ablation electrode 9 is connected with a sub-control unit 6 for controlling the ablation electrode 9 via an electrical connection 61 being, for example, a cable. The sub-control unit 6 and the ultrasound control unit 5 are integrated in a control unit 7. In other embodiments, the control units can be separate control units. Furthermore, the sub-control unit 6 is preferentially further adapted to control a steering of the catheter tip 19 and/or an irrigation. In this case, the catheter further comprises a steering element and/or an irrigation element, respectively, which are not shown in FIG. 1 or FIG. 2. The different control functions can be performed by any number of control units, for example, by a single control unit or by two or more than two control units.

The ultrasound region 50 of the housing 16 is mechanically connected with the ultrasound unit 11. In particular, the ultrasound region 50 is preferentially located at the front side of the piezo material 12 and is in direct contact with the second electrode 15 or, if the second electrode forms the ultrasound unit shielding element, the ultrasound region 50 is the second electrode being mechanically coupled to the piezo material 30. The metal layer in the ultrasound region 50 is thin enough so as acoustical waves are not reflected back, but coupled into the cardiac tissue. This metal layer has a thickness, which is preferentially well below a quarter of the wavelength of the acoustical waves, as explained above in more detail. The metal layer is made of gold. In another embodiment, the metal layer can also be made of another metal.

FIG. 4 shows schematically and exemplarily another embodiment of a tip of the catheter 12. The catheter tip shown in FIG. 4 is similar to the catheter tip described above with reference to FIG. 2, except for a gap between the second electrode 15 and the ultrasound region 50 of the housing 16. Accordingly, the second electrode 15 is connected with the electrical connection shielding element of the coaxial cable 17 via an electrical connection 31. If a gap is between the second electrode 15 and the ultrasound region 50 of the housing 16, the thickness of the housing 16 in the ultrasound region 50 is preferentially very small, for example, smaller than 1 µm, further preferred smaller than 500 nm, and even further preferred smaller than 100 nm.

Referring again to FIG. 1, the sensing apparatus 1 further comprises an object influence determination unit 103 for determining the influence of the energy application on the object 4 depending on the ultrasound sensing of the object 4. In particular, the energy application unit 9 is adapted to ablate the object 4, wherein the object influence determination unit 103 is adapted to determine an ablation depth, which may also be regarded as being a lesion boundary, depending on the ultrasound sensing of the object 4. The object influence determination unit 103 is therefore adapted to receive an ultrasound signal from the ultrasound unit 5 and to determine the ablation depth depending on the received ultrasound signal. The determination of the ablation depth will in the following be described in more detail.

If an ultrasound pulse is sent out to the object, the ultrasound pulse is reflected at different depths such that echo signals are received by the ultrasound unit 11. The echo signals, which are generated by reflection of the ultrasound pulse at different depths within the object, form an echo series. An echo series 21 is schematically and exemplarily shown in FIG. 5. By considering the speed of sound and the time, at which an echo is recorded after the ultrasound pulse has been sent out to the object, the echo series can be translated into a dependence of an ultrasound reflection property of the object on the depth within the object. In FIG. 5, the amplitude a of the echo series in arbitrary units, which corresponds to the ultrasound reflection property, is shown depending on the depth d in arbitrary units that corresponds to the time, at which the respective echo has been received after the pulse has been sent out into the object.

In this embodiment, the object is a wall of a heart, wherein the ultrasound pulse is sent out into the heart tissue of the wall. In FIG. 5, the regions of the echo series 21 denoted by 22 and 23, correspond to front and back surfaces of the heart wall. The region 24 is directly generated by the ultrasound pulse. Thus, in a strict sense, the echo series is the graph shown in FIG. 5 without region 24.

The echo series 21 shown in FIG. 5 allows determining the position of the front and back surfaces 22, 23 with respect to the position of the ultrasound unit 11 that emits the ultrasound pulse and receives the echoes. The first measured amplitude in the region 24 marks the position of the ultrasound unit 11. Region 24 is followed by a region comprising an amplitude being substantially zero and after a while the amplitude increases again in region 23 marking the first reflection at the object, i.e. marking the front surface of the object. A region 25 comprising smaller amplitudes that correspond to reflections within the tissue of the heart wall follows, and then in the region 22 the amplitude increases again significantly thereby marking the back surface of the heart wall. Thus, the echo series 21 allows determining the positions of the front and back surfaces based on the regions 22 and 23. The region 25 in between is used for determining the ablation depth as will be explained further below.

The object influence determination unit 103 is preferentially adapted to determine the position of the increasing amplitude in region 23 after a region comprising an amplitude value being substantially zero as the position of the front surface of the object. Then, the amplitude substantially decreases in region 25 and the position of the next significant increase of the amplitude (region 22) is determined as the position of the back surface of the heart wall. In other words, after the ring down of the transducer of the ultrasound unit in region 24 a "quiet period" ensues. This quiet period is subsequently terminated by a reflection in region 23 that is associated to the front surface. After this reflection in the region 23 a period 25 occurs that is marked by fast and small temperature changes in the ultrasound intensity. In particular, the envelope of the signal in the period 25 tends to have an exponential decrease in intensity. At the end of the period 25 again a strong reflection is observed in the region 22 that is associated to the back surface. Threshold values can predefined, in particular relative threshold values can be predefined, wherein the front surface is detected, if a reflection after the "quiet period" exceeds the respective predefined threshold and wherein the back surface is detected, if at the end of period 25 the signal exceeds the respective threshold. The thresholds can be predefined by calibration measurements with walls having known front surface and back surface positions.

The echo series 21 exemplarily shown in FIG. 5 has been generated by an ultrasound pulse that was sent out into the object at a certain time. Several of these ultrasound pulses are sent out to the object at different times, thereby generating echo series at different times. These echo series, which are obtained from different ultrasound pulses at different times, and, thus, which belong to different times, form dynamic echo series. The ultrasound signal which depends on the received dynamic echo series represents therefore the ultrasound reflection properties of the object at different depths and at different times. Such an ultrasound signal is schematically and exemplarily shown in FIG. 6.

In FIG. 6, different amplitudes of the ultrasound signal are indicated by different brightness, wherein a higher brightness corresponds to larger amplitude. The amplitude is shown depending on the depth d and the time t at which the respective echo series has been generated. The ultrasound signal shown in FIG. 6 forms an image that can be regarded as M-mode image.

By performing an ablation procedure, a lesion is generated in the heart wall, wherein the ablation depth is defined by the boundary of the lesion within the heart wall tissue.

The object influence determination unit is adapted to determine discontinuities in the ultrasound signal and to determine the ablation depth as a depth of the ultrasound signal at which the discontinuities occur. For example, in FIG. 6 in the first ellipse 26 only continuous variations of the ultrasound signal are present indicating a macroscopic tissue expansion of the heart wall tissue during applying ablation energy to the tissue. In the second ellipse 27 discontinuities in the variation of the ultrasound signal can be observed that indicate the ablation depth. Thus, FIG. 6 shows the progression of the lesion, i.e. the increasing ablation depth, in the second ellipse 27. Based on the observed discontinuities the ablation depth is determined as indicated exemplarily for a certain time by the second double arrow 29, whereas the first double arrow 28 indicates the thickness of the heart wall for a certain time. Also the thickness of the heart wall changes with time during performing an ablation procedure due to a macroscopic tissue expansion as can be seen in FIG. 6. For more details regarding the determination of the ablation depth reference is made to WO 2010/082146 A1, which is herewith incorporated by reference.

The sub-control unit 6 is preferentially adapted to control the ablation electrode 9 depending on the ablation depth determined by the object influence determination unit 103. For example, the power and/or duration of applying ablation energy to the object 4 are controlled depending on the determined ablation depth. The object influence determination unit 103 can be adapted to determine the position of a front surface and a back surface of the heart wall from the ultrasound signal and to determine the thickness of the heart wall depending on these positions, i.e. the corresponding depth positions are subtracted from each other to determine the thickness of the heart wall. The sub-control unit 6 can then be adapted to control the ablation electrode 9 depending on this determined thickness and the determined ablation depth. Preferentially, the sub-control unit 6 is adapted to ablate the heart wall tissue until a desired degree of transmurality of the heart wall tissue is reached, in particular, until the resulting lesion is transmural.

Preferentially, the sensing apparatus 1 is adapted to determine the thickness of the heart wall and the ablation depth repeatedly, wherein the ablation depth determination unit 103 is adapted to determine repeatedly a degree of transmurality of ablation from the determined thickness and the determined ablation depth. In particular, the sensing apparatus 1 is adapted to terminate an ablation procedure, if a predetermined degree of transmurality of ablation has been reached.

The sensing apparatus 1 further comprises a visualization unit 20 for visualizing the ablation depth. In particular, the visualization unit 20 is adapted for visualizing the progression of a lesion boundary. The visualization is preferentially performed in real-time. The visualization unit 20 is preferentially adapted to show the ultrasound signal, the progression of ablation, i.e. the lesion boundary, and the front and back surface positions.

The sensing apparatus 1 is preferentially used in combination with a system for determining the position and/or orientation of the catheter 12, in particular, within the object 4, preferably, within a heart of a human being or an animal. In this embodiment, an imaging system like a magnetic resonance image system or an X-ray fluoroscopy system is used for determining the position and/or orientation of the catheter. This imaging system is indicated by the broken line 8 shown in FIG. 1. The catheter 12, in particular, the catheter tip can comprise elements for facilitating the determination of the orientation and/or position of the catheter by using the imaging system 8. For example, the catheter tip can comprise a tracking coil, if the catheter tip is used within a magnetic resonance imaging system, or elements that can be identified on an X-ray image and that are shaped such that a determination of the position and/or orientation of the catheter by using an X-ray fluoroscopy system is possible. The catheter tip can also comprise a location sensor for determining the position and/or orientation of the catheter 12, in particular, of the catheter tip within the object 4.

The positioning systems allows a user to position the catheter 12 within the heart, or more specifically, in the left atrium, of a patient. The user can position the catheter 12 in the correct position with respect to the heart wall to measure the wall thickness using the ultrasound signal generated by the ultrasound unit 11 and the object influence determination unit 103. By using the determined position of the catheter it is possible to display the thickness of the heart wall in an image of the heart. After collecting sufficient measurements, i.e. after determining the thickness of the heart wall at different locations on the heart wall, the user can then establish an ablation strategy including required power and duration depending on the determined heart wall thickness. It is also possible to use the catheter tip for tracing over the prior-performed ablation lesions for verification purposes. The continuity and depth of the lesions that have been created can be determined.

In the following an embodiment of a sensing method for sensing an object is exemplarily described with respect to a flowchart shown in FIG. 7.

The catheter tip 19 comprising the ultrasound unit 11 and the energy application unit 9 has been introduced into a heart 4 of a human being or of an animal for ablating heart wall tissue, wherein the position of the catheter tip 19 has been determined. In step 201 the ultrasound unit 11 sends ultrasound pulses out into the heart wall tissue, receives dynamic echo series after the ultrasound pulses have been reflected by the heart wall tissue, and generates the ultrasound signal depending on the received dynamic echo series.

In step 202, the object influence determination unit 103 determines the thickness of the heart wall tissue at the position of the catheter tip 19, and in step 203 ablation parameters are determined based on the determined thickness of the heart wall tissue. This determination of the ablation parameters can be performed automatically, for example, by using predefined ablation parameters, which are stored in a storing unit and which are assigned to different heart wall tissue thicknesses, and may be some further parameters influencing the selection of the ablation parameters, for example, the desired shape of the lesion, the location of the desired lesion within the heart, the age of the patient et cetera. Ablation parameters are, for example, the power and/or duration of the application of ablation energy. Furthermore, as an ablation parameter a degree of transmurality is defined by a user or automatically determined, for example, by using a look-up table stored in a storing unit. The determination of the ablation parameters can be performed by, for example, the sub-control unit 6 or the object influence determination unit 103.

In step 204, the ablation procedure starts and, while the heart wall tissue is ablated, the ultrasound unit 11, which is shielded by the ultrasound unit shielding element 16 electrically connected to the energy application unit 9, produces ultrasound signals which are used by the object influence determination unit 103 for determining the ablation depth and thickness of the heart wall tissue. Furthermore, in step 204 the ablation depth and the thickness of the heart wall tissue are visualized on the visualization unit 20. During the ablation procedure, the object influence determination unit calculates the degree of transmurality and checks in step 205 whether the degree of transmurality defined in step 203 has been reached. If this is the case, the ablation procedure and preferentially also the ultrasound monitoring stop in step 206. If the defined degree of transmurality has not been reached, the ablation procedure and the determination of the ablation depth and the thickness of the heart wall tissue continue.

Steps 201 to 203 can be omitted, i.e. the catheter tip 12 can already be arranged at the desired location and energy can be applied to the object by the electrical energy application unit, in particular, by the ablation electrode, while the ultrasound unit, which is shielded by an ultrasound unit shielding element electrically connected to the electrical energy application unit, ultrasonically senses the object.

A major drawback in known catheter ablation procedures for cardiac arrhythmias is a lack of adequate information about the lesion quality while the lesion is created. The therapist often relies on his own expertise to determine the optimal ablation parameters such as the power, the temperature and the duration of applying the power. The optimal parameters for ablation very largely, for example, due to intra- and inter-patient differences of, for instance, the thickness of the local heart wall, the local cooling by blood flow, the contact between the catheter and the cardiac tissue, et cetera. A more adequate control of catheter ablation procedures, in particular, of RF catheters, is therefore desired. The above described sensing apparatus can be adapted to provide a real-time feedback of the lesion development in the cardiac tissue, and can provide real-time information about the depth of the lesion with respect to the thickness of the cardiac tissue at the treatment's site. This can prevent injury and death from underheating and/or overheating in catheter ablation procedures. The high-frequency ultrasound can be used to monitor the progression of the lesion boundary in M-mode imaging.

If RF ablation is performed simultaneously with ultrasound imaging using an ultrasound transducer integrated in the tip of the RF ablation catheter a capacitive coupling of the RF signal into the ultrasound signal can generally result. The RF signal can interfere with the ultrasound signal such that tissue reflections are hardly visible in M-mode images generated from the interfered ultrasound signal, because amplitudes of variations in the ultrasound signal caused by the interference by the RF signal are generally much larger than amplitudes of the ultrasound signal caused by reflections of ultrasound waves by the cardiac tissue. The sensing apparatus of the present invention can be adapted to comprise an ultrasound transducer and an ablation electrode within an ablation catheter such that the effect of the RF interference is decreased, without adversely affecting the ultrasound signal.

The frequency of the RF catheter ablation signal can be about 450 kHz. The real-time ultrasound lesion monitoring is preferentially performed with center frequencies being larger than 10 MHz. For example, the center frequency is about 20 MHz. However, RF signal generators may generate high-frequent harmonics which can significantly affect the ultrasound signal within the bandwidth of the ultrasound transducer used for the real-time lesion assessment. The sensing apparatus is therefore preferentially adapted such that the influence of the RF ablation signal on the ultrasound signal is as small as possible and preferably within the ultrasound signal noise level. A corresponding catheter comprising the ablation electrode and the ultrasound transducer can work in combination with many RF signal generators. Furthermore, if desired a digital filtering can be used for filtering remaining influences of the RF signal on the ultrasound signal out of the ultrasound signal, without adversely affecting the RF ablation procedure.

The sensing apparatus can be adapted as a cardiac ablation monitoring catheter which can be used in combination with an RF signal generator. However, the sensing apparatus can also be adapted to sense other objects like other parts of a person or of an animal such as another organ or vessels, or a technical object like a pipeline. Moreover, instead of applying RF energy, the electrical energy application unit can also be adapted to apply other electrical energy to the object.

Although in the embodiment described above with reference to FIG. 2 the catheter comprises an energy application unit and an ultrasound unit only, the catheter can also comprise further elements like further sensing elements and/or further energy application elements, irrigation elements, et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Determinations like the determination of the ablation depth or of a heart wall thickness performed by one or several units or devices can be performed by any other number of units or devices. For example, the determination of the ablation depth or of the heart wall thickness can be performed by a single unit of by any other number of different units. The determinations and/or the control of the sensing apparatus in accordance with the above described sensing method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A sensing apparatus for sensing an object, the sensing apparatus (1) comprising:

an ultrasound unit (11) for ultrasonically sensing the object (4), an electrical energy application unit (9) for applying electrical energy to the object (4), an ultrasound unit shielding element (16) for electrically shielding the ultrasound unit (11) from the electrical energy applied to the object, wherein the ultrasound unit shielding element (16) is electrically connected to the electrical energy application unit (9).

2. The sensing apparatus as defined in claim 1, wherein the sensing apparatus (1) comprises a catheter (12), wherein the ultrasound unit (11), the electrical energy application unit (9) and the ultrasound unit shielding element (16) are integrated in the catheter (12).

3. The sensing apparatus as defined in claim 1, wherein the electrical energy application unit (9) is an electrode for applying electrical energy to the object (4) and wherein the electrode (9) is electrically connected to the ultrasound unit shielding element (16).

4. The sensing apparatus as defined in claim 1, wherein the ultrasound unit (11) comprises at least two connection electrodes (14, 15), wherein a first connection electrode (14) is electrically connected to a control electrical connection (40) for connecting the ultrasound unit (11) with an ultrasound control unit (5) for controlling the ultrasound unit (11) and a second electrode (15) of the ultrasound unit (11) is electrically connected to an electrical connection shielding element (42) for shielding the control electrical connection (40).

5. The sensing apparatus as defined in claim 1, wherein the electrical connection shielding element (42) has a resistance being smaller than 5Ω.

6. The sensing apparatus as defined in claim 1, wherein the ultrasound unit (11) comprises at least two connection electrodes (14, 15), wherein a first connection electrode (14) is electrically connected to a control electrical connection (40) for connecting the ultrasound unit (11) with an ultrasound control unit (5) for controlling the ultrasound unit (11) and a second electrode (15) of the ultrasound unit (11) is electrically connected to the ultrasound unit shielding element (16).

7. The sensing apparatus as defined in claim 1, wherein the ultrasound unit shielding element (16) is a housing enclosing the ultrasound unit (11) for electrically shielding the ultrasound unit (11).

8. The sensing apparatus as defined in claim 7, wherein the ultrasound unit (11) and the housing (16) are arranged such that ultrasound waves are emittable and/or receivable through an ultrasound region (50) of the housing (16).

9. The sensing apparatus as defined in claim 8, wherein the ultrasound unit (11) is operable at an ultrasound frequency defining an ultrasound wavelength in the ultrasound region (50) of the housing (16) and wherein at least in the ultrasound region (50) the housing (16) has wall with a thickness being smaller than a quarter of the ultrasound wavelength.

10. The sensing apparatus as defined in claim 8, wherein the ultrasound region (50) is mechanically connected with the ultrasound unit (11).

11. The sensing apparatus as defined in claim 1, wherein the sensing apparatus (1) further comprises an object influence determination unit (103) for determining the influence of the energy application on the object (4) depending on the ultrasound sensing of the object (4).

12. The sensing apparatus as defined in claim 11, wherein the energy application unit (9) is adapted to ablate the object (4) and wherein the object influence determination unit (103) is adapted to determine an ablation depth depending on the ultrasound sensing of the object (4).

* * * * *